(12) United States Patent
Barth et al.

(10) Patent No.: US 8,764,192 B2
(45) Date of Patent: Jul. 1, 2014

(54) OPHTHALMOLOGICAL EXAMINATION DEVICE

(75) Inventors: Roland Barth, Jena (DE); Frank Behrendt, Jena (DE); Roland Bergner, Jena (DE); Klaus-Ditmar Voigt, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 208 days.

(21) Appl. No.: 12/513,098

(22) PCT Filed: Nov. 13, 2007

(86) PCT No.: PCT/EP2007/009793
§ 371 (c)(1),
(2), (4) Date: Apr. 30, 2009

(87) PCT Pub. No.: WO2008/058699
PCT Pub. Date: May 22, 2008

(65) Prior Publication Data
US 2010/0053554 A1    Mar. 4, 2010

(30) Foreign Application Priority Data
Nov. 17, 2006 (DE) .......................... 10 2006 054 774

(51) Int. Cl.
| A61B 3/107 | (2006.01) |
| A61B 3/15  | (2006.01) |
| A61B 3/117 | (2006.01) |
| A61B 3/00  | (2006.01) |
| A61B 3/10  | (2006.01) |

(52) U.S. Cl.
CPC ............... *A61B 3/152* (2013.01); *A61B 3/0041* (2013.01); *A61B 3/107* (2013.01); *A61B 3/117* (2013.01); *A61B 3/1005* (2013.01)
USPC ........... 351/208; 351/211; 351/212; 351/214; 351/246

(58) Field of Classification Search
CPC .... A61B 3/107; A61B 3/1005; A61B 3/0041; A61B 3/0016; A61B 3/152; A61B 3/15; A61B 3/117
USPC .......... 351/205, 206, 208, 214, 211–212, 246
See application file for complete search history.

(56) References Cited

U.S. PATENT DOCUMENTS

| 3,718,386 | A |   | 2/1973  | Lynn et al.              |
| 4,436,388 | A | * | 3/1984  | Takahashi et al. 351/206 |
| 4,861,155 | A |   | 8/1989  | Downey                   |
| 4,917,458 | A | * | 4/1990  | Matsumura 351/212        |
| 5,463,430 | A |   | 10/1995 | Isogai et al.            |

(Continued)

FOREIGN PATENT DOCUMENTS

| DE | 35 41 726 A1  | 5/1987  |
| DE | 197 15 212 A1 | 10/1997 |

(Continued)

*Primary Examiner* — Zachary Wilkes
(74) *Attorney, Agent, or Firm* — Patterson Thuente Pedersen, P.A.

(57) ABSTRACT

An opthalmological measuring instrument, e.g. for determining the corneal curvature, anterior chamber depth, axial length, or the like, including measuring systems for determining measurement of the mentioned physical parameters. The measuring systems are connected to an evaluation unit which verifies whether quality parameters regarding the measurements are satisfied and generates a corresponding signal that indicates to the medical professional user that a proper measurement can be taken.

17 Claims, 1 Drawing Sheet

(56) References Cited

U.S. PATENT DOCUMENTS

| | | | |
|---|---|---|---|
| 5,625,428 A * | 4/1997 | Isogai | 351/208 |
| 5,835,190 A | 11/1998 | Miyake | |
| 5,905,562 A | 5/1999 | Isogai et al. | |
| 5,988,815 A * | 11/1999 | Maus et al. | 351/221 |
| 6,386,706 B1 | 5/2002 | McClure et al. | |
| 6,621,917 B1 | 9/2003 | Vilser | |
| 6,779,891 B1 * | 8/2004 | Barth et al. | 351/212 |
| 7,322,699 B2 | 1/2008 | Barth et al. | |
| 7,377,643 B1 * | 5/2008 | Chock et al. | 351/208 |
| 7,404,641 B2 | 7/2008 | Michelson et al. | |
| 2002/0052551 A1 | 5/2002 | Sinclair et al. | |
| 2005/0119642 A1 * | 6/2005 | Grecu et al. | 606/5 |

FOREIGN PATENT DOCUMENTS

| | | |
|---|---|---|
| DE | 198 57 001 A1 | 6/2000 |
| DE | 103 13 975 A1 | 11/2003 |
| WO | WO 98/23202 | 6/1998 |

* cited by examiner

OPHTHALMOLOGICAL EXAMINATION DEVICE

PRIORITY CLAIM

The present application is a National Phase entry of PCT Application No. PCT/EP2007/009793, filed Nov. 13, 2007, which claims priority from German Application Number 102006054774.8, filed Nov. 17, 2006, the disclosures of which are hereby incorporated by reference herein in their entirety.

The invention relates to an opthalmological examination device, with which measurements are taken and documented.

BACKGROUND OF THE INVENTION

During the examination of the eye of a patient, measurements are frequently taken, the results of which are documented, and which, therefore, must be reproducible.

Among others, these include corneal curvature, anterior chamber depth, iris diameter (e.g., according to the white-to-white method), and the length of the ocular axis. In order for these measurements to be reproducible, it is particularly important, aside from the measuring accuracy, that during the measuring procedure, the measuring instrument is positioned precisely and reproducibly with regard to the patient's eye.

From U.S. Pat. No. 5,463,430, a keratometer is known, whereby two different marking systems are used for determining the correct measuring distance. At first, a circular reference marking is reflected in the optical path, whereby its apparent diameter should correspond with the average diameter of a patient's cornea. With said marking, the operator determines the alignment and, roughly, the correct distance of the patient's eye to the measuring instrument. Subsequently, a more precise determination of the distance is made in such a way that parts of the index marking system, intended for the actual measuring, are projected onto the cornea as "finite" as well as "infinite." For the switch between "finite" and "infinite," a collimator lens is occasionally removed from the optical path of the projection; for the actual measurement, said lens has to be realigned. When the correct distance is set, the measuring process is triggered automatically, which is indicated to the operator through a color change of the circular reference marking.

In U.S. Pat. No. 5,905,562, it is suggested that the axial alignment is determined through projection of an additional measuring marking onto the cornea, subsequent mapping of the resulting image and evaluation through image processing; determination of the measuring distance is carried out the same way as in U.S. Pat. No. 5,463,430. In this example, the measurement is also triggered automatically once correct alignment has been ascertained.

Said solutions exhibit a number of disadvantages. For example, the determination of the measuring distance through the necessary realignment of the collector lens is time-consuming and can, therefore, lead to incorrect measuring results in case of a movement by the patient; furthermore, additional mechanical requirements are necessary.

Experience has also shown that automatic triggering of the measurement in said solutions does not always produce optimal results, in accordance with prior art, since, e.g., the imaging of the eye can be distorted through eye lashes protruding into the optical path of the measuring instrument, insufficiently developed tear film, etc., which may lead to faulty measurements. Said conditions cannot be recognized by the solutions of prior art; therefore, automatic triggering may take place even if unsuitable measuring conditions are present, which, in turn, may lead to incorrect measurements, and which, in principle, are difficult to recognize or even completely unrecognizable as such.

SUMMARY OF THE INVENTION

The invention is based on the task of overcoming the disadvantages of prior art and to introduce an opthalmological measuring instrument, which provides precise measurement results even under unfavorable conditions.

This task, according to the invention, is solved with an opthalmological measuring instrument, wherein the measuring systems are connected to an evaluation unit, which verifies adherence to quality parameters regarding measurements and generates a respective signal.

The method, according to the invention, for the operation of the opthalmological measuring instrument is characterized in that the measuring systems carry out several measuring processes in a row, wherein quality parameters are determined for every measurement, and said quality parameters are verified by an evaluation unit. If said verification determines that a proper measurement is possible, a signal is generated, which indicates to the user that now the actual measurement can be triggered. Preferably, said signal can be an optical signal, e.g., color change of a display or by means of an additional display. However, it is also possible for said signal to be of an acoustic or tactile nature. Thereby, after the evaluation of the quality parameters has shown that a proper measurement should be possible, the user is given the opportunity to use his/her experience and consider other conditions in his/her decision for triggering the final measurement, which were not taken into consideration or were not to be considered during the automatic determination of the quality parameters.

In the following, the invention will be further explained with the use of a preferred embodiment, an opthalmological measuring instrument for measuring corneal curvature and the anterior chamber depth. The measuring principle and the design of such a device are, for example, shown in detail in patent application DE 19 857 001, the entire contents of which is hereby incorporated by reference.

DETAILED DESCRIPTION

Figure 1:
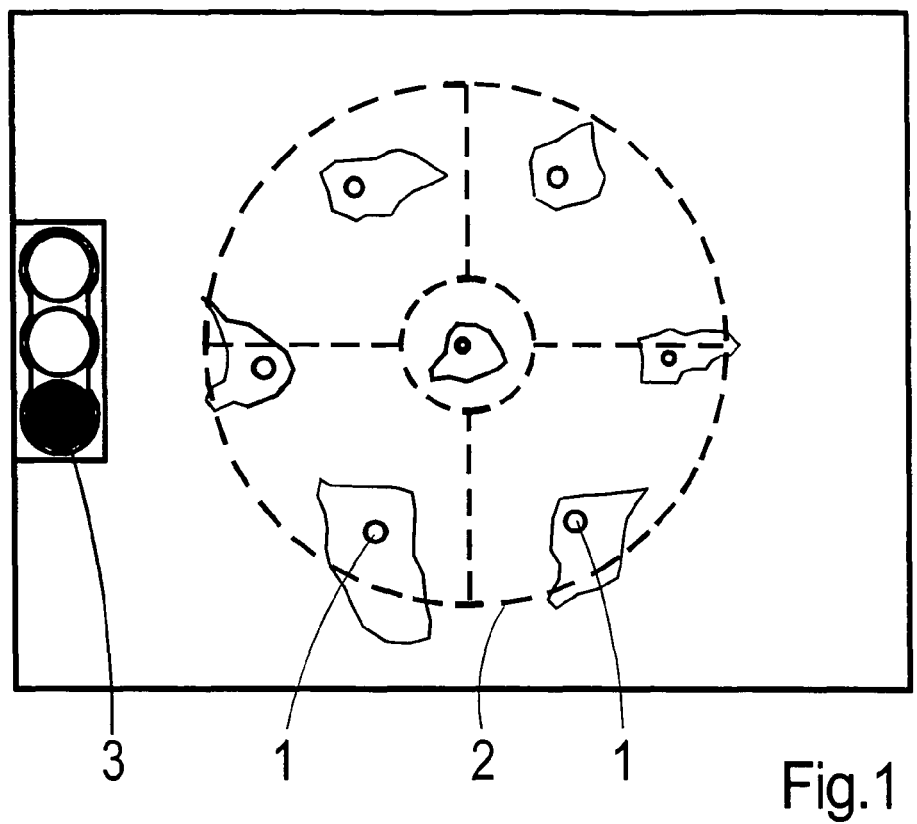
FIG. 1 depicts a keratometer (corneal curvature measurement) measuring mode as graphically presented to an operator in accordance with the invention.

Keratometer:

FIG. 1 shows the measuring mode as graphically presented to the operator at his console.

The eye is illuminated with six IR light emitting diodes. The light reflected from the cornea is mapped onto a CCD camera, and from the distances of the point-shaped reflex images 1, the corneal radii are calculated.

These six measuring markings 1 are used for an internal automatic determination of the measuring quality.

For determining measuring distance z, the size of the images of the individual measuring markings is ascertained as function of the corneal radius. Thereto, several measurements (e.g., 10 times per second) are taken during the alignment process and each time the images of the six reflex images 1 are evaluated. For said evaluation, radius, area, and circumference of the reflex images, for example, are determined mathematically (if necessary, in accordance with a prior threshold value determination) and examined according to predefined criteria.

Thereby, focusing, i.e., the distance for the sharpest image through search for the minimum of the areas of the reflex images 1, is determined.

In order to determine the x/y coordinates, a measuring window 2, herein depicted circularly, is defined on the image, which is provided by the CCD camera; all six reflex images must be located within said measuring window 2.

In order to ensure that insufficient tear film, drooping eye lids or lashes do not influence the measuring markings, a shape detection is carried out for the six reflex images 1. Thereby, e.g., roundness, circumference, and energy/brightness are determined, and a comparison of said properties between each of the six images is performed.

Subject to the fulfillment of defined criteria, for example, a signal in the form of a "traffic light" 3, which is displayed on the operator console, is switched from red via yellow to green. Thereby, red means that no proper measurement can be performed, in which case the triggering of the measuring process can also be prevented; the green light indicates that a proper measurement is possible and the user can, therefore, trigger it.

Criteria for the switch of the "traffic light" to "yellow" are, e.g.: The standard deviation of the areas of the individual reflex images 1 is less than 25%; or the standard deviation of the circumferences is less than 20%. For "green," the respective standard deviations must be less than 15% and 10%, respectively.

It is also possible to perform the automatic triggering of at least one measurement on "green" if the user forgoes his/her own evaluation.

Alternatively, it is possible to constantly perform a measurement of the corneal radius and save it, together with the quality criteria, in order to choose the best measurement, based on the quality criteria, at a later date. Said selection can, once again, be carried out automatically through mathematical evaluation of the quality criteria.

Anterior Chamber Depth

Figure 2:
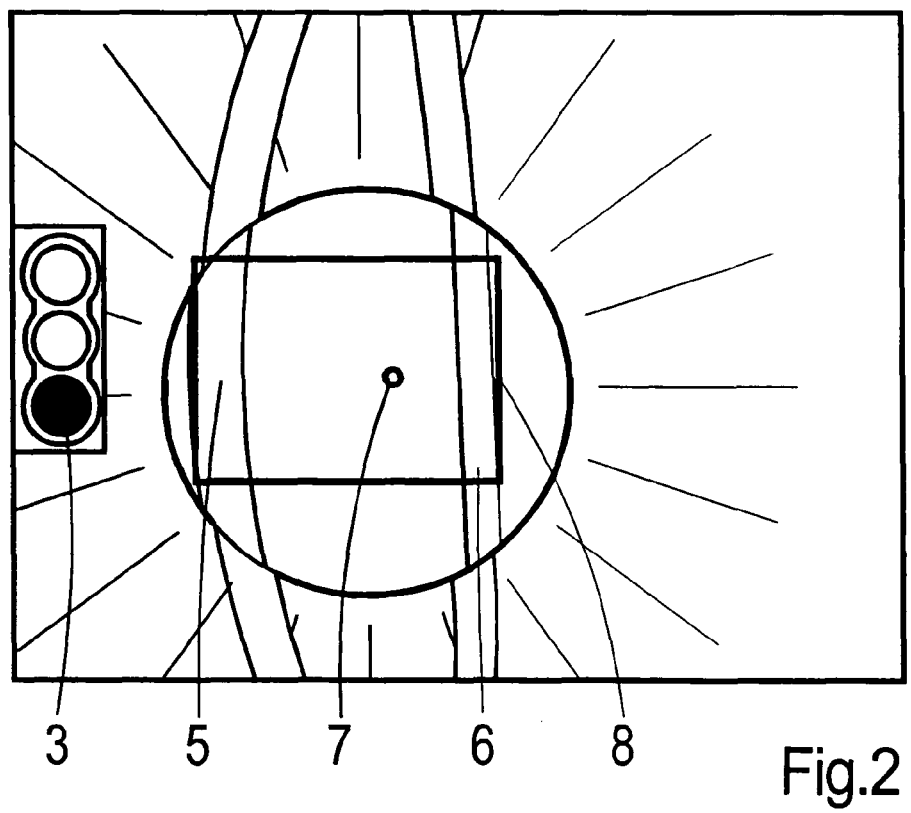
FIG. 2 depicts an anterior chamber depth measuring mode as graphically presented to an operator in accordance with the invention.

FIG. 2 also shows how the measuring mode appears on the operator display.

The eye is illuminated from the side through a light slit. The resulting light sections on the eye (cornea 5, lens 6) are mapped onto a CCD camera. The patient looks straight at an LED, resulting in light reflex 7, which is also mapped onto the CCD camera.

Said light sections 5, 6 and the reflex point 7 are used for the automatic determination of the measuring quality.

In order to determine the x/y coordinates, a measuring window 8 is defined in the image provided by the CCD camera and must contain the light sections 5, 6 and the image of the fixation point 7.

In order to determine the measuring distance z, the size of the image of the individual reflex point 7 is ascertained as function of the corneal radius. Thereto, several measurements (e.g., 10 times per second) are taken during the alignment process, and the following analyses are carried out:

In order to correctly align the device with the eye of the patient, position and size of the image of the individual point 7 (image of the fixation point) in relation to the light sections 5, 6 are monitored (it must be positioned between corneal section 5 and lens section 6); furthermore, it is ascertained whether the corneal section is free of additional reflexes. For the size of the image of the reflex point 7, an expected value can be determined from the previously determined corneal radius (see keratometer measurement); the adherence to said expected value can also be used as criterion.

Subject to the adherence to said criteria, a "traffic light" 3, which is shown on the operator display, is, once again, switched from red via yellow to green, thereby signaling the user to trigger the measurement.

The invention is not bound to the depicted embodiments; particularly, for other measurements, respective criteria can be established and monitored without deviating from the scope of protection of the patent claims.

The invention claimed is:

1. An ophthalmological measuring instrument, for determining measurements of a physical parameter of an eye of a patient, comprising:

measuring systems that are structured to measure numerical values that represent corneal curvature of the eye, wherein the measuring systems are connected to an evaluation unit which verifies whether quality parameters regarding the measurements are satisfied; and generates a corresponding signal indicating whether the quality parameters are satisfied;

wherein the measurement is based on an image of reflected image points from the cornea that are located within a measurement window defined in the image provided by a camera; and further wherein the quality parameters verified include a size and a shape of the reflected image points within the measurement window defined in the image provided by the camera; and the ophthalmological measuring instrument including structure that presents the corresponding signal to a medical professional operating the ophthalmological measuring instrument.

2. The ophthalmological measuring instrument, according to claim 1, wherein the signal that is presented to the medical professional is selected from a group consisting of optical, acoustic, or tactile.

3. The ophthalmological measuring instrument, according to claim 1, wherein the measurement results and the quality parameters ascertained from the individual measurements are saved thereby making the measurement results and the quality parameters available for future evaluation.

4. The ophthalmological measuring instrument, according to claim 1, wherein the instrument presents a choice to the medical professional user as to whether to trigger the instrument thereby leaving the decision for triggering the measurement in the event of a positive signal to the medical professional user.

5. The ophthalmological measuring instrument, according to claim 1 wherein the instrument automatically triggers the measurement in the event of a positive signal.

6. The ophthalmological measuring instrument, according to claim 1, wherein the instrument prevents triggering of the measurement until a positive signal is ascertained.

7. A machine implemented method of operating an ophthalmological measuring instrument comprising:

carrying out several measurements in a row with measuring systems structured to determine measurements of physical parameters of an eye, the measurements being of numerical values that represent corneal curvature and anterior chamber depth of the eye;

determining quality parameters for each measurement;

verifying said quality parameters by utilizing an evaluation unit; and signaling the results of said verification such that the results are perceptible to a medical professional user of the ophthalmological measuring instrument determining the corneal curvature from an image of reflected image points from the cornea that are located within a first measurement window defined in the image provided by a camera; and determining the quality parameters that are related to corneal curvature verified based on a size and a shape of the reflected image points within the first measurement window defined in the image provided by the camera;

determining the anterior chamber depth from an illuminated slit and further wherein the quality parameter requires that the light sections including a first light section of parts of the cornea and a second light section of parts of the crystalline lens that bound the anterior chamber are located in a second measurement window defined in the image provided by the camera and further wherein the quality parameters related to anterior chamber depth includes a position and a size of a reflected image of a fixation point relative to the light sections.

8. The method, according to claim 7, further comprising saving the measurement results and the quality parameters ascertained from the individual measurements thereby making the measurement results and the quality parameters available for future evaluation.

9. The method, according to claim 7, further comprising presenting a choice to the medical professional user as to whether to trigger the instrument thereby leaving the decision for triggering the measurement in the event of a positive signal to the medical professional user.

10. The method, according to claim 7, further comprising automatically triggering the measurement in the event of a positive signal.

11. The method, according to claim 7, further comprising preventing the triggering of the measurement until a positive signal is ascertained.

12. An ophthalmological measuring instrument, for determining measurements of a physical parameter of an eye of a patient, comprising:

measuring systems that are structured to measure numerical values that represent anterior chamber depth-of the eye, wherein the measuring systems are connected to an evaluation unit which verifies whether quality parameters regarding the measurements are satisfied and generates a corresponding signal indicating whether the quality parameters are satisfied;

wherein the anterior chamber depth is measured based on an image of light sections from an illuminated slit and further wherein the quality parameters require that the light sections including a first light section of parts of the cornea and a second light section of parts of the crystalline lens that bound the anterior chamber and are located in a measurement window defined in the image provided by a camera and further wherein the quality parameter includes a position and a size of a reflected image of a fixation point relative to the light sections; and the ophthalmological measuring instrument including structure that presents the corresponding signal to a medical professional operating the ophthalmological measuring instrument.

13. The ophthalmological measuring instrument, according to claim 12, wherein the signal that is presented to the medical professional is selected from a group consisting of optical, acoustic, or tactile.

14. The ophthalmological measuring instrument, according to claim 12, wherein the measurement results and the quality parameters ascertained from the individual measurements are saved thereby making the measurement results and the quality parameters available for future evaluation.

15. The ophthalmological measuring instrument, according to claim 12, wherein the instrument presents a choice to the medical professional user as to whether to trigger the instrument thereby leaving the decision for triggering the measurement in the event of a positive signal to the medical professional user.

16. The ophthalmological measuring instrument, according to claim 12, wherein the instrument automatically triggers the measurement in the event of a positive signal.

17. The ophthalmological measuring instrument, according to claim 12, wherein the instrument prevents triggering of the measurement until a positive signal is ascertained.

* * * * *